United States Patent
Chinn et al.

(10) Patent No.: US 6,725,096 B2
(45) Date of Patent: Apr. 20, 2004

(54) MULTIPLE IN-LINE CONTACT CONNECTOR

(75) Inventors: Kenny K. Chinn, Rosemead, CA (US); Grace Ying Yang Jang, Calabasas, CA (US); Stephen L. Goldman, Stevenson Ranch, CA (US); Donald L. Sandford, Northridge, CA (US); B. Reno Lauro, Stevenson Ranch, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 151 days.

(21) Appl. No.: 09/818,380

(22) Filed: Mar. 27, 2001

(65) Prior Publication Data

US 2002/0143376 A1 Oct. 3, 2002

Related U.S. Application Data

(60) Provisional application No. 60/202,259, filed on May 5, 2000.

(51) Int. Cl.[7] .................................................. A61N 1/04
(52) U.S. Cl. ........................ 607/115; 439/299; 439/909
(58) Field of Search .......................... 439/91, 261, 282, 439/298, 299, 310, 312, 345, 352, 372, 675, 676, 669, 783, 864, 909; 600/373, 382, 393; 607/115, 37, 38, 117

(56) References Cited

U.S. PATENT DOCUMENTS

| | | | |
|---|---|---|---|
| 4,186,988 A | 2/1980 | Kobler ........................ 339/176 |
| 4,712,557 A | 12/1987 | Harris ........................ 128/419 |
| 4,715,380 A | 12/1987 | Harris ........................ 128/419 |
| 4,774,950 A | * 10/1988 | Cohen ...................... 128/419 D |
| 4,995,389 A | 2/1991 | Harris ........................ 128/419 |
| 5,274,917 A | * 1/1994 | Corbett, III et al. .......... 29/860 |
| 5,354,326 A | 10/1994 | Comben et al. ............. 607/115 |
| 5,368,496 A | 11/1994 | Ranalletta et al. .......... 439/261 |
| 5,560,358 A | * 10/1996 | Arnold et al. ............... 128/642 |
| 5,904,580 A | 5/1999 | Kozel et al. .................. 439/66 |
| 5,919,213 A | * 7/1999 | Nelson et al. .................. 607/8 |
| 6,198,969 B1 | 3/2001 | Kuzma ......................... 607/37 |
| 6,205,361 B1 | 3/2001 | Kuzma et al. .............. 607/116 |
| 6,321,126 B1 | * 11/2001 | Kuzma ....................... 607/137 |

* cited by examiner

Primary Examiner—Jeffrey R. Jastrzab
Assistant Examiner—Frances P. Oropeza

(57) ABSTRACT

A tool-less connector with multiple contacts and a compact design is provided. Therefore, a connector that is normally tunneled through body tissue will now require only a minimally invasive subcutaneous tunnel, which should reduce tissue healing time, patient discomfort, and risk of infection. In addition, providing additional contacts allows enhanced stimulation protocols. One embodiment of the present invention provides a connector pin containing multiple in-line contacts. Each "line" consists of a row of independent contacts arranged in a linear array running along the long axis of the pin. In other embodiments of the invention, the mating receptacle of the connector allows for multiple contacts while minimizing the space required for the increased number of contacts. Additional embodiments provide features that, for instance, prevent the contacts on the connector pin to touch the contacts in the receptacle until all contacts are appropriately aligned.

22 Claims, 14 Drawing Sheets

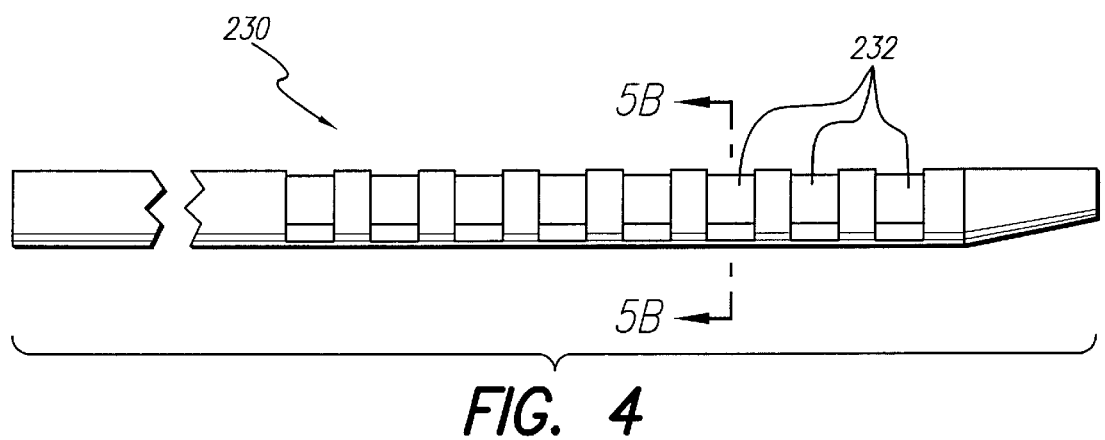
FIG. 4
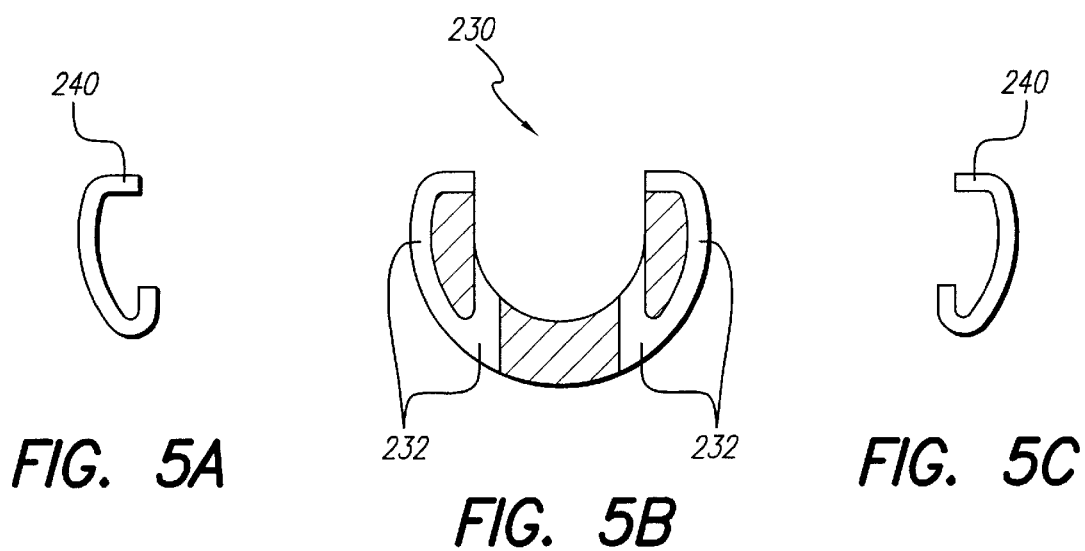
FIG. 5A
FIG. 5B
FIG. 5C
FIG. 5D

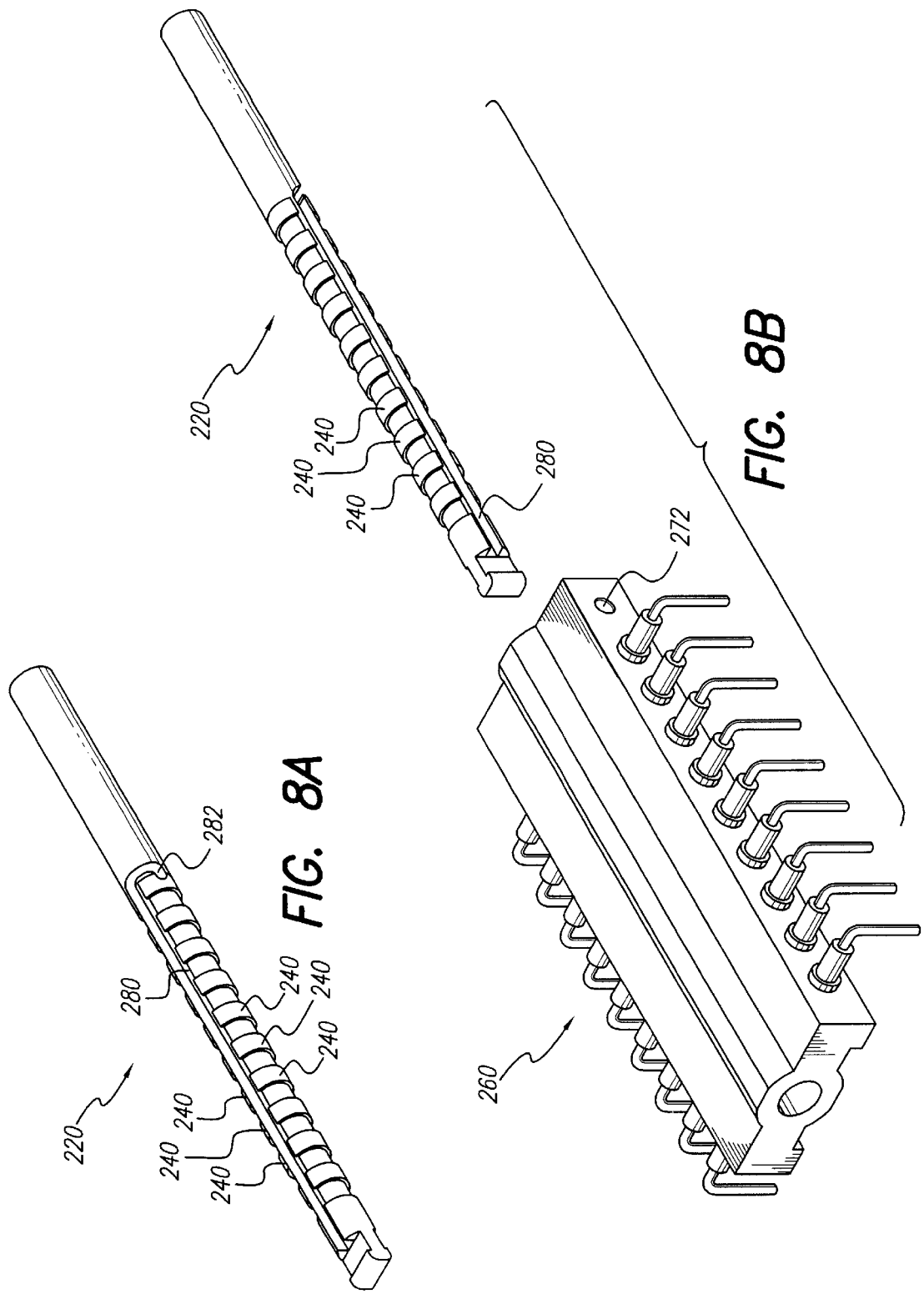

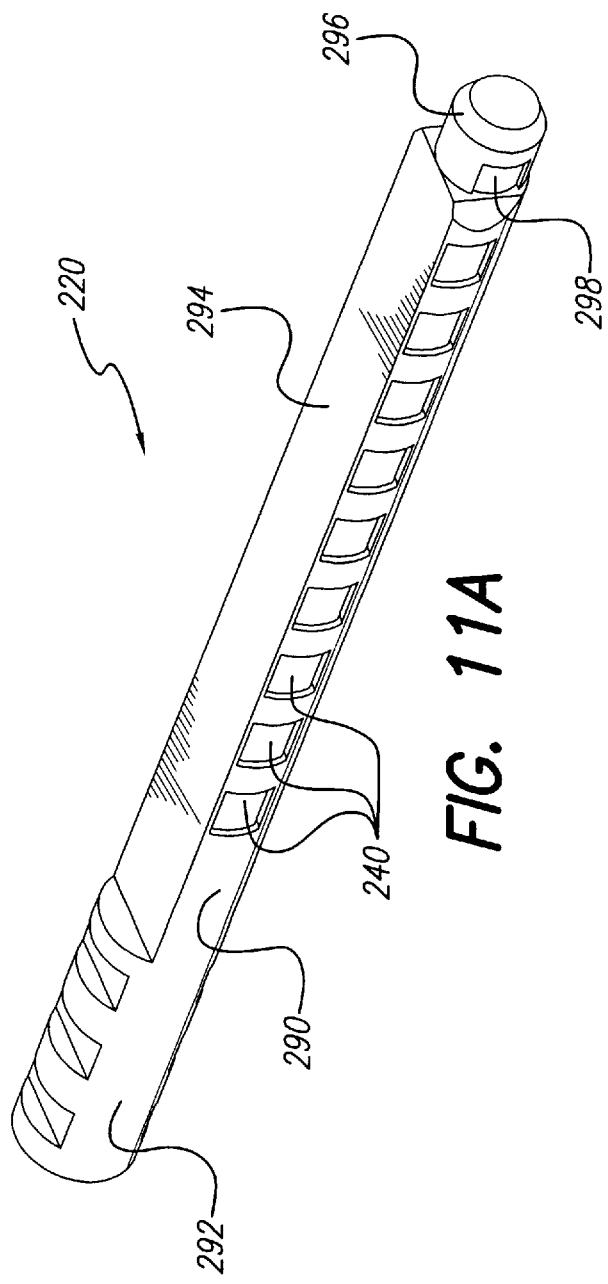
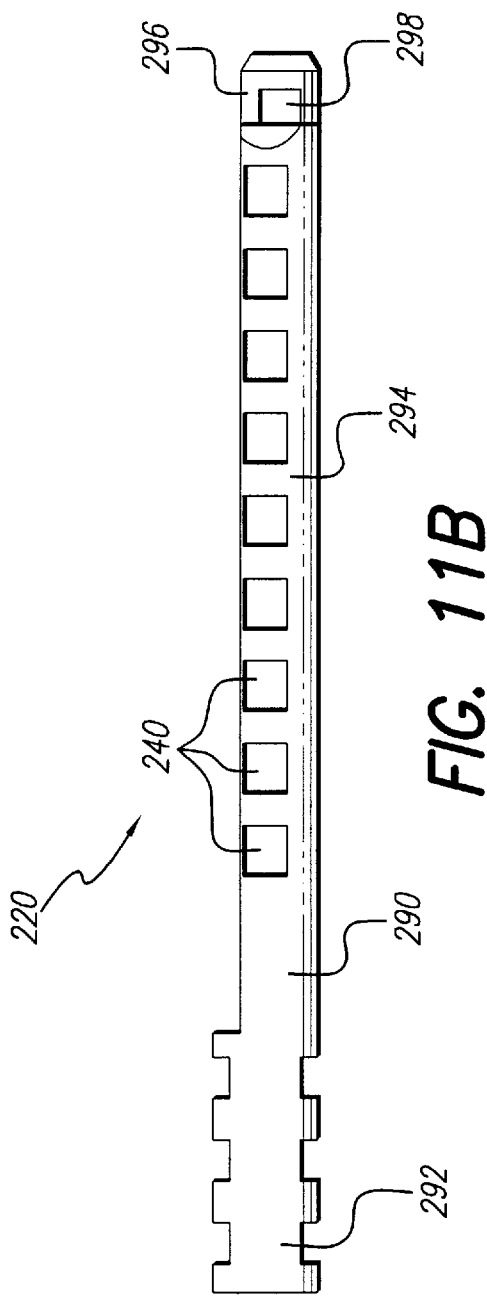
FIG. 11A
FIG. 11B

MULTIPLE IN-LINE CONTACT CONNECTOR

This application claims the benefit of U.S. Provisional Application Serial No. 60/202,259, filed May 05, 2000, which application is incorporated herein by reference in its entirety.

FIELD OF THE INVENTION

The present invention generally relates to a medical device for stimulating tissue in a living body, and more particularly relates to a multi-contact connector for use with such medical devices.

BACKGROUND OF THE INVENTION

A variety of neurostimulation systems include an array of electrodes, formed on a lead, that are electrically connected to an implanted electronic package. Often, the electrical connection is achieved in part via one or more lead extensions that connect to the electronic package at a proximal end and connect to the lead carrying the electrode array at a distal end (and together with the lead carrying the electrode array, may be called a lead system). For instance, for a typical neurostimulation system, the proximal end of one or more lead extensions is connected to an implanted pulse generator, while the distal end of the lead extension(s) connects to one or more leads bearing electrode arrays, which electrodes are positioned in the spinal column.

For many neurostimulation systems, it is common to perform a "trial stimulation" wherein the electrodes are positioned at the target location, while a pulse generator remains external to the patient during the trial period. For a number of days, the patient's response to a variety of stimulation parameters is gauged, prior to performing the surgical procedure of implanting the pulse generator in the patient's body. If the patient's response to the trial stimulation is not acceptable, the pulse generator is simply not implanted, and only the electrode array/lead system needs to be removed.

For the trial stimulation period, a lead extension commonly called a percutaneous lead extension connects, at its distal end, to the proximal end of the electrode array lead. The percutaneous lead extension lies in a tunnel through body tissues and extends outside the body, where its proximal end is connected (possibly via an additional external cable) to an external "trial stimulator."

A typical surgical process for implanting a trial stimulation system includes first using an electrode insertion needle to implant the electrode array so that the electrodes are positioned at the target stimulation site. The electrode insertion needle is a hollow needle preferably carrying a removable solid-core stylet. After the needle is situated, the stylet is removed, leaving a hollow opening. To ensure the needle tip has entered the epidural space, a loss of resistance procedure is typically employed.

To prevent damage to the electrode array, a lead blank that approximates the diameter of the electrode array lead may be inserted into the needle to clear away any tissue obstructing the path through the needle and into the epidural space. The lead blank is then removed and the electrode array is passed through the needle and cleared path into the epidural space.

When the series of electrodes are in the general vicinity of the target, the physician fine-tunes placement by connecting the electrode array to an external trial stimulator and soliciting patient feedback of paresthesia for each electrode. After the electrode array is properly positioned, the needle must be removed, either by pulling it out over the end of the electrode array's lead, or by disassembly if the connector at the proximal end of the electrode array is larger than the needle. With the array positioned at the target site, the surgeon secures the lead by making an incision near the point where the lead enters the spine. The lead is secured at that point via a lead anchor.

The physician then creates a tunnel between the anchored, proximal end of the electrode array and the percutaneous exit site (i.e., the location where the percutaneous lead extension exits the body through the skin). At the incision where the lead is anchored, the distal end of the percutaneous lead extension is connected to the proximal end of the electrode array. A tunneling tool is used to create the tunnel from the percutaneous exit site to this same incision. The proximal end of the percutaneous lead extension is attached to the tunneling tool, which pulls the proximal end of the extension back through the tunnel as the tool is removed, and out through the percutaneous exit site. The proximal end of the percutaneous extension, now protruding through the skin, is connected to the trial stimulator cable (possibly via an additional external cable).

The percutaneous extension preferably has a small connector at its proximal end to minimize the diameter of the tunnel through which the extension is pulled. The larger the tunnel, the more tissue trauma, post surgical pain, recovery time, and possibility of infection.

In addition, for some patients, two electrode arrays are used. With current designs, the surgeon typically creates a separate subcutaneous tunnel for each percutaneous extension. It would be a great advantage to need only one extension and one subcutaneous tunnel.

Additionally, current connector designs typically have four or eight contacts per connector pin. To increase the number of contacts per connector, a connector with two (or more) pins is typically used. This is often referred to as a dual connector.

A need exists for more compact electrical connections, both inside and outside the body. In addition, a need exists for a greater number of contacts per connector, without increasing the size of the connector or space required for the connector receptacle within an electronic package.

BRIEF SUMMARY OF THE INVENTION

In view of the above, it would be preferable to have a single percutaneous extension with a proximal connector having, for example, 16 contacts on one small-diameter pin. The number of subcutaneous tunnels would preferably be reduced to one, and the size of the tunnel required to draw the connector through the tunnel would also preferably be minimized.

The receptacle portion of the connection currently faces the same limitation regarding number of contacts versus connector size. For instance, available 16-contact connectors result in a receptacle size that greatly impacts the overall size of an electronic package. By creating a receptacle that accepts a connector with a single small-diameter 16-contact pin, the electronic device size is significantly reduced.

Other connection points within a trial stimulation setting and within a "permanent" stimulation setting can benefit from a design with the improvements described herein. For instance, connections within the body, such as between the electrode array lead or internal extension and the implanted pulse generator, are generally quite bulky, especially for 16-contact (16-electrode) configurations.

As such, the invention disclosed and claimed herein provides a tool-less connector with multiple contacts and a compact design. As a result, using this connector, e.g., within a trial stimulator setting, a minimally invasive subcutaneous tunnel can be created which should reduce tissue healing time, patient discomfort, and infection risk. Advantageously, providing additional contacts allows enhanced stimulation protocols and/or additional channels for other purposes, such as for feedback. In some embodiments of the invention, the mating receptacle of the connector allows for multiple contacts while minimizing the space required for the increased number of contacts.

One embodiment of the present invention provides a connector pin containing multiple in-line contacts. Each "line" consists of a row of independent contacts arranged in a linear array spaced along the long axis of the pin. Each contact is connected to a conductor that lies within the pin. Each conductor extends out through the end of the pin and into a cable. This cable may be the body of a percutaneous lead extension, an internal lead extension, or any of a number of other components within a trial or "permanent" stimulation setting.

In other embodiments of the present invention, a receptacle is provided that has contacts arranged to align with the matching contacts on the connector pin.

Additional embodiments of the invention provide contacts that may be in the form of spring loaded pins or leaf-style springs.

Yet other embodiments of the invention provide features that prevent the contacts on the connector pin from touching the contacts on the receptacle until all contacts are appropriately aligned.

Thus, the present invention provides connector pins that allow, inter alia, the diameter of a tunnel created for a percutaneous lead extension to be minimized. By reducing the tunnel diameter, recovery time, patient discomfort, and possibility of infection are reduced. Using subject connectors/receptacles in other system locations offers similar advantages due to the decreased area affected by the surgery and the implanted components.

Other advantages of the present invention include (but are not limited to) decreased size of any electrical device that houses a receptacle for a subject connector, access to a greater number of simulation alternatives or other use of additional channels, enhanced pin-to-receptacle contact schemes, and tool-less operation of the connection. The connector pins of the present invention may be used advantageously wherever an electrical connection is required, such as between the percutaneous extension and any external cable, between the percutaneous extension and the trial stimulator, and/or between the fully implanted extension and the implanted pulse generator.

BRIEF DESCRIPTION OF THE DRAWINGS

The above and other aspects, features, and advantages of the present invention will be more apparent from the following more particular description thereof, presented in conjunction with the following drawings wherein:

FIG. 4 is a side view of the body of the pin of FIG. 3;

FIG. 5A is an end view of a contact of the pin of FIGS. 2–4;

FIG. 5B is a section view through line 5B—5B shown in FIG. 4;

FIG. 5C is an end view of a contact of the pin of FIGS. 2–4;

FIG. 5D is a trimetric view of a contact of the pin of FIGS. 2–4;

FIG. 8A is a trimetric view of a connector pin of an exemplary embodiment of the present invention;

FIG. 8B is a trimetric view of the receptacle of FIGS. 7A–7C and the connector pin of FIG. 8A;

FIG. 11A is a trimetric view of a connector pin of another exemplary embodiment of the present invention;

FIG. 11B is a side view of the pin of FIG. 11A;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
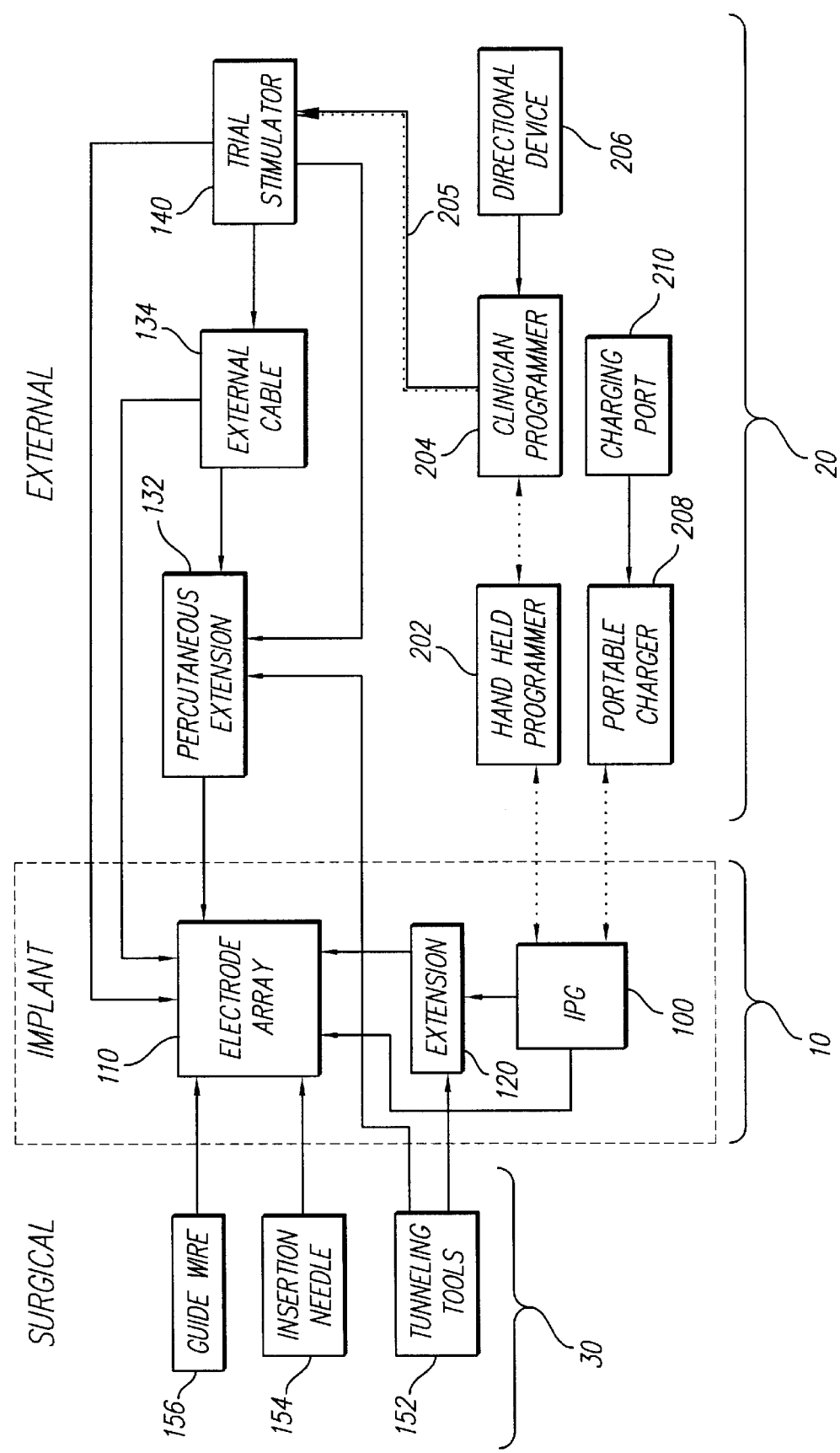
FIG. 1A is a block diagram that illustrates an exemplary system that can benefit from the present invention.

For illustration purposes, the following description of the present invention is shown in conjunction with a Spinal Cord Stimulation (SCS) system. The SCS system depicted via a block diagram in FIG. 1A illustrates an exemplary system that can benefit from the present invention. As will be apparent to those of skill in the art, the present invention may be applied to other systems, whether or not the system components are intended to be implanted into a living body. Any components intended to be used in a surgical situation must be capable of sterilization for use within an operating room (OR), and more preferably, may be sterilized with ethylene oxide (ETO). In addition, non-biocompatible components intended to be implanted are preferably hermetically sealed (e.g., processor chip(s) and related components of an implantable pulse generator (IPG)), and any surfaces of components that will interface with body tissues and/or fluids must be made of biocompatible materials (e.g., the container for the components of the IPG).

The components of the SCS system shown in FIG. 1A may be subdivided into three broad categories: (1) implantable components 10, (2) external components 20, and (3) surgical components 30. As seen in FIG. 1A, the implantable components 10 include an implantable pulse generator (IPG) 100, an electrode array 110, and (as needed) a lead extension 120. The stimulation is delivered via electrode array 110. Extension 120 may be used to electrically connect the electrode array 110 to IPG 100, if the lead containing the electrodes (i.e., the electrode array 110) is not long enough to reach the IPG implantation site.

In a preferred embodiment, IPG 100 comprises a rechargeable, multichannel, 16-contact (or more), telemetry-controlled pulse generator housed, for instance, in a rounded titanium enclosure. The connector receptacle of the present invention preferably forms an integral part of IPG 100, allowing electrode array 110 or extension 120 to be detachably secured and electrically connected to IPG 100. As will be understood by those of skill in the art, the connectors/receptacles of the present invention, when implanted, must be sealed (i.e., electrically isolated) to protect electrical connections from shorting.

IPG 100 preferably contains stimulating electrical circuitry ("stimulating electronics"), a power source (e.g., a rechargeable battery), and a telemetry system. Typically, IPG 100 is placed in a surgically-made pocket either in the abdomen, or just at the top of the buttocks. It may, of course, be implanted in other locations of the patient's body. Once implanted, IPG 100 is connected to the lead system, comprising one or more lead extensions 120, if needed, and at least one electrode array 110. Lead extension 120, for example, may be tunneled up to the spinal column. Once implanted, electrode array(s) 110 and lead extension(s) 120 are intended to be permanent. In contrast, IPG 100 may be replaced when its power source fails or is no longer rechargeable, or as improved models become available.

Figure 1B:
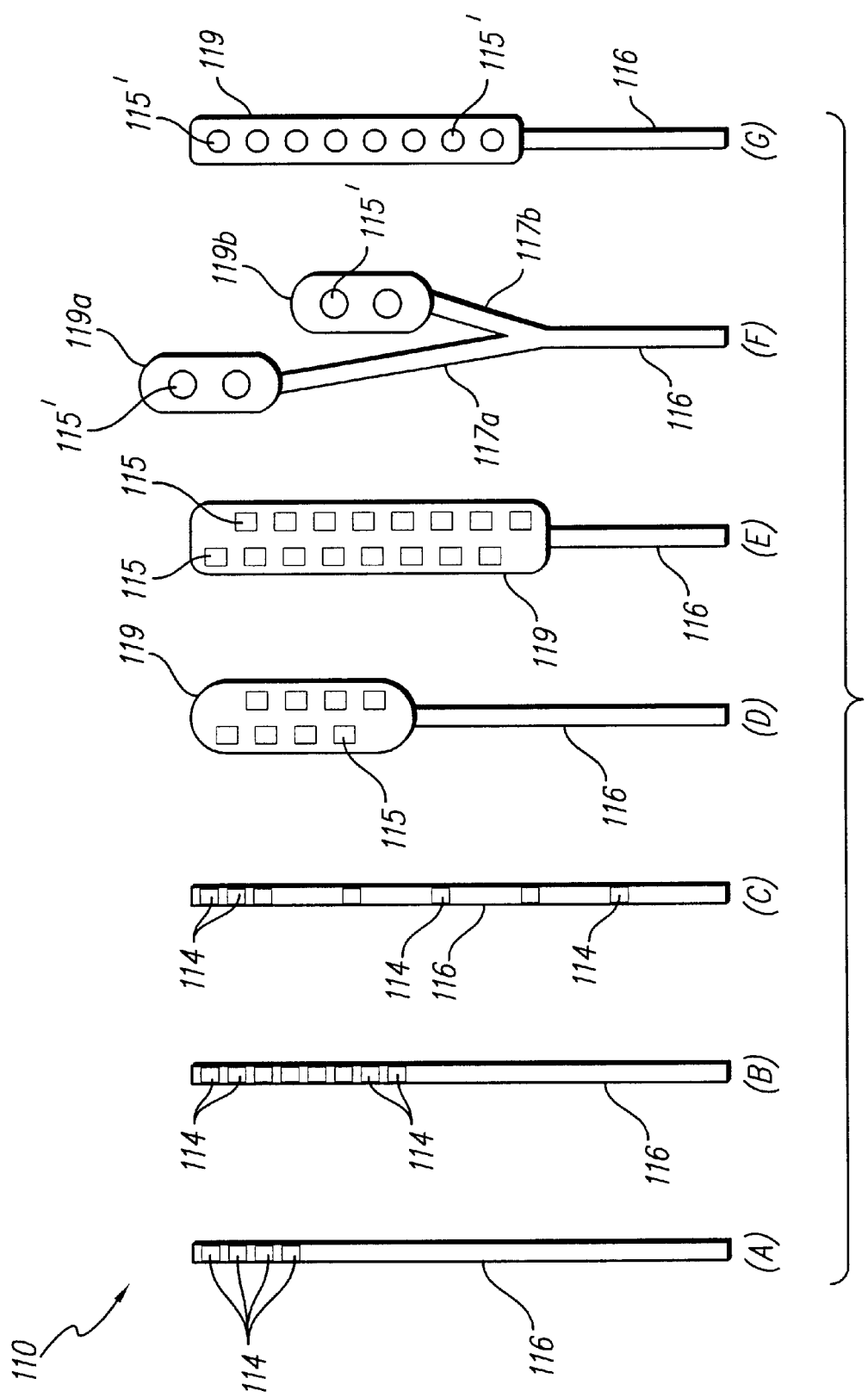
FIG. 1B illustrates examples of various types of electrode arrays that may be used with the present invention.

Advantageously, IPG 100 can provide electrical stimulation through a multiplicity of electrodes (e.g., sixteen electrodes) included within the electrode array(s) 110. Different types of electrode arrays 110 that may be used with the invention are depicted in FIG. 1B. A common type of electrode array 110 is the "in-line" lead, as shown at (A), (B), and (C) in FIG. 1B. An in-line lead includes individual electrodes 114 spread longitudinally along a small diameter flexible cable or carrier 116. The flexible cable or carrier 116 carries small wires embedded (or otherwise carried) therein from each electrode to a proximal end of the lead (not shown), where such wires may be electrically connected to IPG 100 (or to a lead extension 120, which in turn connects to IPG 100).

An advantage of an in-line lead is its ease of implantation, i.e., it can be inserted into the spinal canal through a small locally-anesthetized incision while the patient is kept awake. When the patient is awake, he or she can provide valuable feedback of paresthesia for a given electrode or electrodes 114 for a given positioning of the array 110. Note, as used herein, the term "paresthesia" refers to that area or volume of the patient's tissue that is affected by the electrical stimuli applied through the electrode array. The patient may typically describe the paresthesia as an area where a tingling sensation is felt.

To overcome migration problems often associated with in-line electrodes, a different type of electrode array 110 may be used, known as a paddle lead. Various types of paddle leads are illustrated at (D), (E), (F) and (G) of FIG. 1B. In general, each type of paddle lead is shaped with at least one wide platform 119 on which a variety of electrode configurations or arrays are situated. For instance, lead (F) of FIG. 1B has two platforms 119a and 119b, at the end of lead branches 117a and 117b, respectively. Electrodes may be in a variety of shapes and configurations. For example, leads (D) and (E) in FIG. 1B have two columns of longitudinally staggered, rectangular-shaped electrodes 115. Arrays of circular-shaped electrodes 115' are shown in (F) and (G) of FIG. 1B. As also seen in FIG. 1B, the electrodes may vary in number and spacing, as well as shape and orientation.

Still other types of leads may be used with IPG 100 in addition to the representative leads shown in FIG. 1B. For example, the deployable electrode array disclosed in U.S. Pat. No. 6,205,361 represents a type of lead and electrode array that may be used with the invention. The '361 patent is incorporated herein by reference in its entirety.

Whichever type of lead and electrode array is used, an important feature of the exemplary SCS system is the ability to support one or more leads with two or more channels. Here, a "channel" is defined as a specified electrode, or group of electrodes, that receives a specified pattern or sequence of stimulus pulses. Having multiple channels that may be connected to multiple electrodes, positioned within one or more electrode arrays so as to cover more tissue/nerve area, greatly facilitates providing the type of stimulation pattern and stimulation parameters needed to treat a particular patient.

Figure 1C:
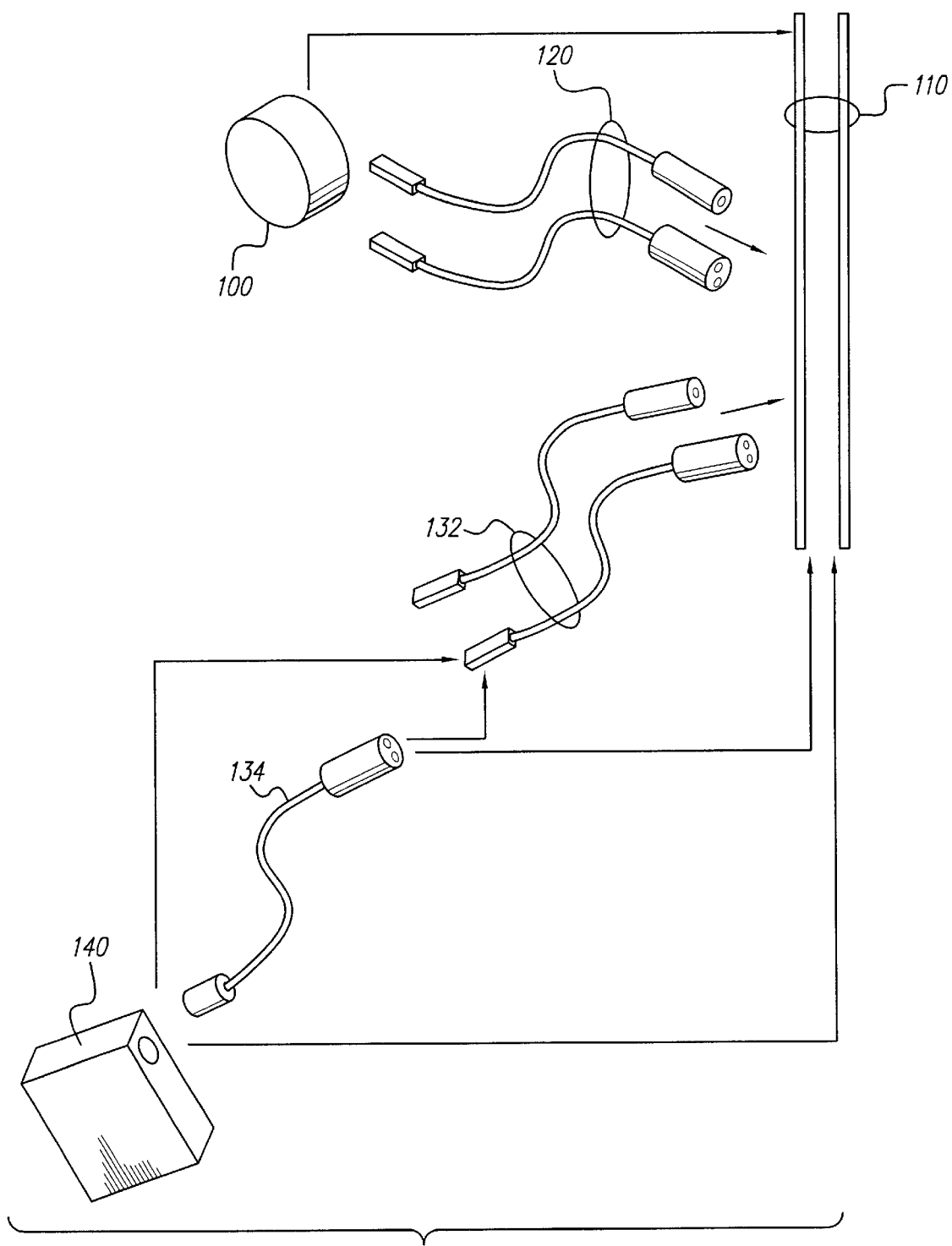
FIG. 1C shows various components that interface with the implantable electrode arrays of FIG. 1B or with other arrays.

As seen in FIGS. 1A and 1C, electrode array 110 and its associated lead system typically, but not necessarily, interface with the implantable pulse generator (IPG) 100 via a lead extension 120. As needed, e.g., for testing and/or fitting purposes, electrode array 110 may also interface with an external trial stimulator 140. Electrode array 110 may interface directly with trial stimulator 140, or the connection may be made via one or more percutaneous lead extensions 132 and/or through one or more external cable leads 134. In this manner, the individual electrodes included within electrode array 110 may receive an electrical stimulus from either trial stimulator 140 or IPG 100.

Because of this percutaneous, or "through-the-skin" connection, trial stimulator 140 is also referred to as a "percutaneous stimulator" 140. The main purpose of stimulator 140 is to provide a stimulation trial (typically 2–7 days) with the surgically placed electrode array 110 before implanting IPG 100.

Typically, during implant of the electrode array, when stimulator 140 is under control of a surgeon, stimulator 140 is connected to electrode array 110 through external cable(s) 134 and possibly, but not necessarily, percutaneous extension 132. Then, after implant, during a trial period when stimulator 140 is under control of the patient, stimulator 140 is connected to electrode array 110 directly through percutaneous extension 132. In other words, once the patient leaves the operating room, there is generally no need for external cable(s) 134.

Trial stimulator 140 preferably has circuitry that allows it to perform the same stimulation functions as does IPG 100.

Further, the circuitry within trial stimulator 140 allows it to receive and store programs that control its operation through a suitable communication link 205 (FIG. 1A) with the clinician programmer 204. Thus, with such link 205 established, the clinician programmer 204 may be used to program trial stimulator 140 in much the same way that the clinician programmer is used to program IPG 100, once IPG 100 is implanted. Advantageously, link 205 is bi-directional, thereby allowing programming data sent to the stimulator 140 from clinician programmer 204 to be verified by sending the data, as stored in the stimulator 140, back to programmer 204 from stimulator 140. In one embodiment, link 205 comprises an infra-red (IR) link; in another embodiment, link 205 comprises a cable link.

As suggested in the block diagram of FIG. 1A, percutaneous extension(s) 132 and lead extension(s) 120 are inserted through the patient's tissue through the use of appropriate surgical components 30, and in particular through the use of tunneling tools 152, as are known in the art, or as are especially developed for purposes of spinal cord stimulation systems.

In a similar manner, electrode array 110 is implanted in a desired position, e.g., adjacent the spinal column of the patient, through the use of an insertion needle 154 and, if needed, a guide wire 156. The insertion needle, for example, may be a 15-gauge Touhy needle. Additionally, as required, a lead blank may be used to aid in the insertion process. A lead blank is a somewhat flexible wire that approximates the lead diameter. The lead blank is used to clear the path through the insertion needle and into the epidural space before inserting electrode array 110. Use of the lead blank prevents damage to the electrode array when tissue is obstructing the insertion path.

One manner of using surgical components 30 during an implant operation is described in the above referenced deployable electrode patent, U.S. Pat. No. 6,205,361.

Another exemplary manner of using surgical components 30 (FIG. 1A) during an implant operation of an in-line electrode array may be summarized as follows: A fifteen gauge hollow needle 154 is used to create an opening in the spinal canal to insert an in-line array, e.g., an in-line array of the type shown in FIG. 1B (A), (B), or (C). The hollow needle includes a removable stylet (solid core) for use during the needle insertion. After the needle has been situated, the stylet is removed to reveal the hollow opening through needle 154. To ensure the needle tip has entered the epidural space, a loss of resistance technique (commonly known to those skilled in SCS procedures) would typically be employed.

As described above, a lead blank approximating the diameter of the electrode array may then be inserted into needle 154 to clear away any tissue obstructing the path through the needle and into the epidural space. The electrode array 110 is then passed through the needle into the epidural space.

Next, the surgeon will typically apply stimulation to electrode array 110, soliciting patient feedback of paresthesia, to confirm proper array placement. As stated previously, the electrode array(s) 110 may interface directly with the trial stimulator 140, or the connection may use one or more external cables 134.

After the electrode array 110 position is confirmed, the electrode array needs to be secured. An incision is made adjacent needle 154 so that the needle is visible via the wound. Needle 154 is then removed, preferably by pulling the needle over the proximal end of the lead. Hence, if the connector at the proximal end of the lead is larger than the fifteen gauge needle tube, a split needle, or some other mechanism, must be used to allow removal of the needle over the connector.

A section of the lead containing electrode array 110 is now visible through the wound, where needle 154 was previously visible. The section of the lead visible through the wound is carefully pulled into the wound, followed by the entire proximal end of the lead containing, at its distal end, electrode array 110. Since the connector for electrode array 110 is pulled into the wound, it is preferable that the diameter of the connector be minimized, and most preferably be no larger that the diameter of the lead body. Hence, the present invention may be used advantageously for this connection. Once the lead is pulled through, the proximal end of the electrode array no longer exits the body where needle 154 was inserted, but exits instead through the wound. This is herein called the spinal exit site.

Next, a lead anchor is placed around the electrode array's lead and positioned at the spinal exit site. The anchor is secured in place to prevent movement of the electrode array and its lead.

If additional electrode arrays 110 are implanted, the above procedure may be repeated for each array 110, or multiple needles 154 may be used at one time to implant multiple electrode arrays 110 at the same time.

If a trial stimulation period is to be used, a tunnel is then created between a percutaneous exit site and the spinal exit site. If the lead containing electrode array 110 is not long enough to extend out the percutaneous exit site, one or more percutaneous extension(s) 132 are used to connect electrode array 110 to external trial stimulator 140. As described earlier and shown in FIGS. 1A and 1C, electrode array 110 or percutaneous extension 132 may be connected to the trial stimulator 140 via one or more external cable(s) 134.

The surgeon uses suitable tunneling tools 152 to create a tunnel between a percutaneous exit site and the spinal exit site. According to one alternative, the proximal end of either the electrode array 110 or a percutaneous lead extension 132 is attached to the distal end of the tunneling tool 152. As the tunneling tool 152 is retracted, it pulls the proximal portion of the lead back out through the tunnel as the tool is removed. In another alternative, the tunneling tool 152 deposits a tube in the tunnel created, through which the lead is threaded. The exiting end of the lead may then be connected to either trial stimulator 140 or external cable 134. Additional tunnels are typically created for each electrode array 110.

Any connector that will be pulled or threaded through the tunnel will preferably have a minimal diameter, and preferably a diameter that is no larger than the diameter of the lead. As the tunnel diameter increases, so does patient discomfort, recovery time, and possibility of infection. As such, if the proximal end of the lead containing the electrode array is to be pulled or threaded through the tunnel, the connector at its proximal end will benefit from the present invention. Likewise, if the connector at the distal or proximal end of a percutaneous lead extension is to be pulled or threaded through the tunnel, the present invention may be used to minimize the connector diameter, and thus the tunnel diameter.

Percutaneous extension 132 is typically at least 150 mm in length, but may be as long as about 800 mm. The percutaneous extension diameter is preferably minimized, e.g., no greater than 3 mm in diameter when it connects with a single 8 electrode array, (e.g., an in-line electrode array having eight electrodes, or an electrode of the type shown in FIG. 1B (G)), or preferably no greater than 4 mm in diameter when it connects with a dual-8 electrode array, (e.g., an electrode array of the type shown in FIG. 1B (E)).

If more than one electrode array 110 is implanted, and a percutaneous lead extension 132 is used, it may be preferable to use a connector at the distal end of extension 132 with more than one receptacle, or more preferably, a receptacle that accepts two or more pins. In this manner, the number of subcutaneous tunnels may be reduced. The proximal connector of extension 132 would preferably use the present invention to include contacts for all electrodes in one connector. Thus, the teachings of the present invention may be used in connections with multiple connector pins and multiple receptacles.

Of course, connectors that are not tunneled or threaded through body tissues can also incorporate the teachings of the present invention. For instance, an external cable 134 preferably has a connector based on the present invention, and the trial stimulator 140 preferably has a receptacle based on the present invention. In addition, when link 205 comprises a cable link, it may advantageously use connections described herein for connecting to trial stimulator 140 and clinician programmer 204.

The IPG and related components may similarly incorporate the present invention. For instance, the connector pin(s) at the proximal end of extension 120 are inserted into receptacle(s) in the IPG 100. By using a connector and receptacle of the present invention for this interface, the size of IPG 100 may be reduced, so the surgical pocket for holding IPG 100 may be smaller. In addition, the proposed design, materials, and construction methods of the present invention may reduce the cost of connector receptacles and/or connector pins. Connections that are implanted need to be properly sealed to insulate electrical contacts from shorting. Techniques for sealing connectors and insulating electrical contacts are known to those of skill in the art.

Figure 2:
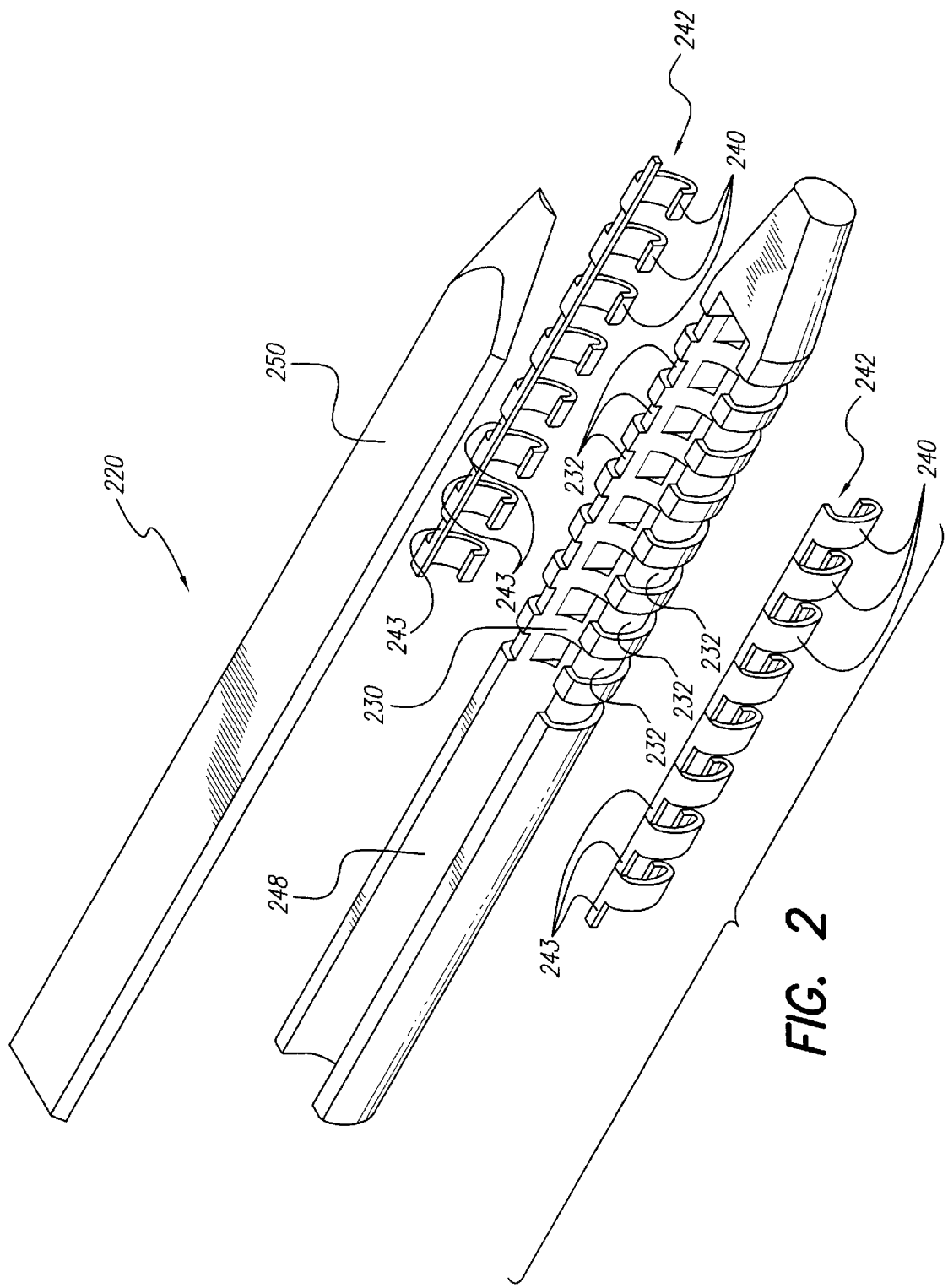
FIG. 2 is an exploded trimetric view of a connector pin of an exemplary embodiment of the present invention.

Turning now to FIG. 2, an exploded view of connector pin 220 of the present invention is shown. Pin body 230 is preferably made of a biocompatible material that is also an electrical insulator, more preferably of polyurethane, silicone, or polytetrafluorethylene (PTFE), and most preferable of epoxy, styrene-butadiene, polysulfone, or the like. Body 230 preferably comprises a tube with an outer diameter of about 3 mm to 4 mm, and more preferably about 3.2 mm, and an inner diameter of about 1.5 mm to 2 mm, and more preferably about 1.7 mm. Body 230 preferably has a channel with an opening at the top along its length of about 1.5 mm to 2 mm wide, and more preferably about 1.7 mm wide.

Figure 3:
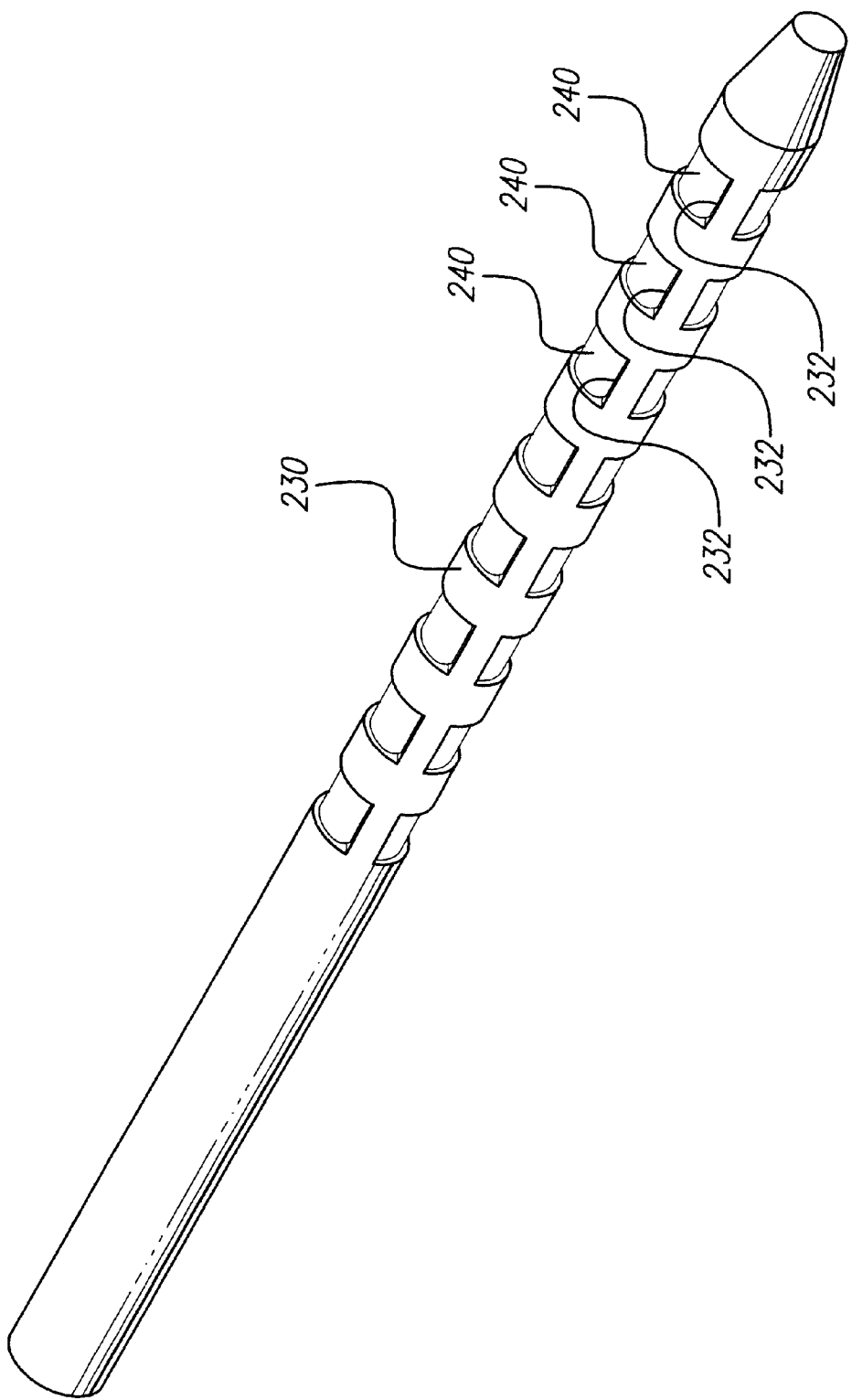
FIG. 3 is a trimetric view of the underside of the assembled body of the pin of FIG. 2.

The end of body 230 tapers to a blunt tip, to ease insertion into a receptacle. Two or more rows of grooves 232 are formed along body 230 where contacts 240 are positioned. For instance, as seen in FIGS. 2 and 3, if two rows of eight contacts each are desired, the end of body 230 preferably has eight grooves 232 along each side. As best seen in FIGS. 4 and 5B, grooves 232 extend from the top, open edge of the tube nearly to the bottom (contacts 240 should not touch at the bottom), then preferably extend into body 230. Therefore, in a preferred embodiment, each contact 240 (FIGS. 5A, 5B, and 5C) wraps around approximately one-third of body 230. However, additional rows of contacts 240 are possible.

Contacts 240 are typically made of, for instance, stainless steel, nickel-plated stainless steel, gold-plated beryllium copper, titanium, tantalum, or noble metal(s) such as platinum or platinum/iridium. The contacts 240 are positioned in grooves 232 via any number of means known to one of skill in the art. For instance, as shown in FIG. 2, each row of contacts may be formed in one piece, as a contact array 242. Each individual contact 240 is then removed from the array, via, e.g., cutting the bridging sections 243 between contacts. Once separated from the array, each contact 240 is pressed or snapped into a groove 232 in pin body 230. For example, in the alternative depicted in FIGS. 4 and 5A–5C, a contact will slide from below into the section of groove 232 through pin body 230, then snap over the lip at the top of body 230.

Each contact 240 is connected to a suitable wire (not shown), which extends out of connector pin 220 through a channel 248 in pin body 230 (FIG. 2). Each wire ultimately connects (possibly through one or more extensions and additional connectors) a contact 240 at a proximal end of the wire to an electrode 114/115/115' or other electrical component (e.g., a sensor) at the distal end of the wire.

Figure 6A:
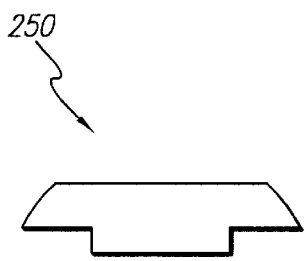
FIG. 6A is an end view of the top section of the pin of FIGS. 2–4.
Figure 6B:
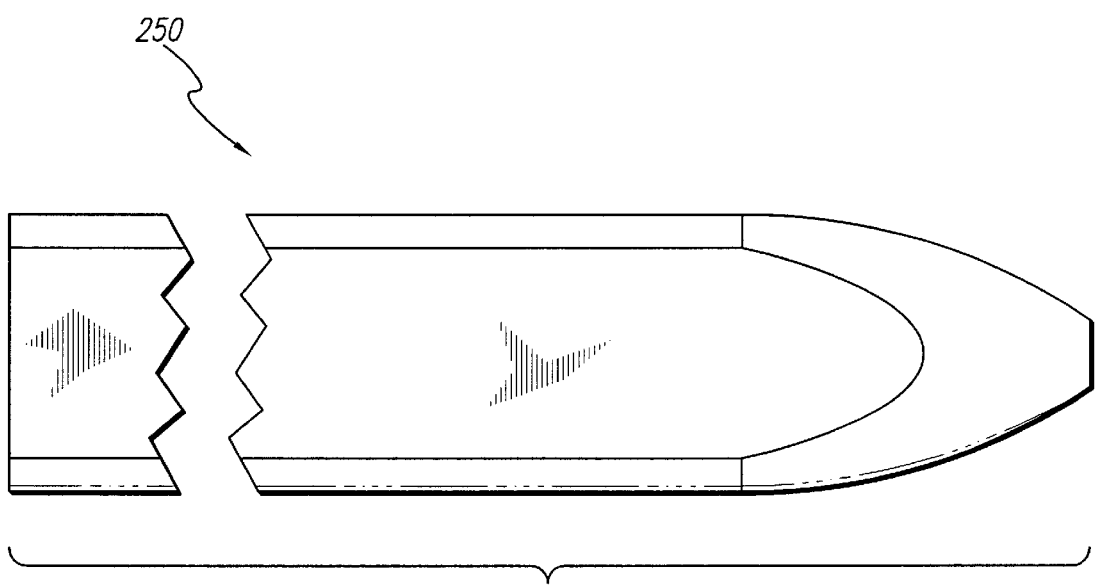
FIG. 6B is a top view of the top section of the pin of FIGS. 2–4.
Figure 6C:
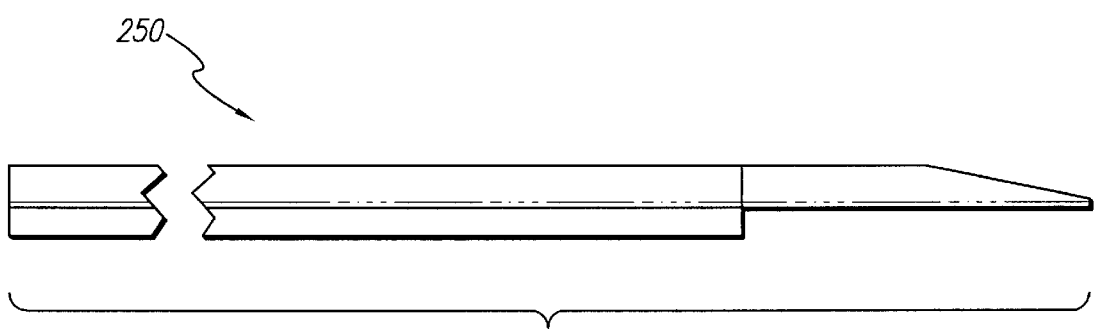
FIG. 6C is a side view of the top section of the pin of FIGS. 2–4.

As seen in FIGS. 2 and 6A–6C, a pin top 250 completes connector pin 220. Pin top 250 is preferably made of the same material as pin body 230. Once contacts 240, with their wires, are assembled along pin body 230, pin top 250 is set on top of body 230. Pin top 250 is preferably secured to body 230 via ultrasonic welding, and more preferably with a medical-grade adhesive. As best seen in FIGS. 6A–6C, top 250 is shaped so that part of the top extends into body 230, which helps hold the wires in place and also forms a better connection and seal.

More preferably, individual contacts 240 and their associated wires are placed into a mold as mold inserts, and the insulating material for pin 220 is then used to fill the mold, which securely affixes contacts 240 to the outside of pin 220. In this case, the wires would be encased in pin 220, which is preferably solid, without a separate pin body 230 and pin top 250. Alternatively, as indicated earlier, each row of contacts may be formed as a contact array 242 (FIG. 2). After molding, bridging sections 243 between contacts 240 are preferably protruding from pin 220, so the contacts are readily separated by removing the bridging sections, via, e.g., cutting. Other alternatives for forming and joining pin 220 and contacts 240 will be apparent to those skilled in the art.

Figure 7A:
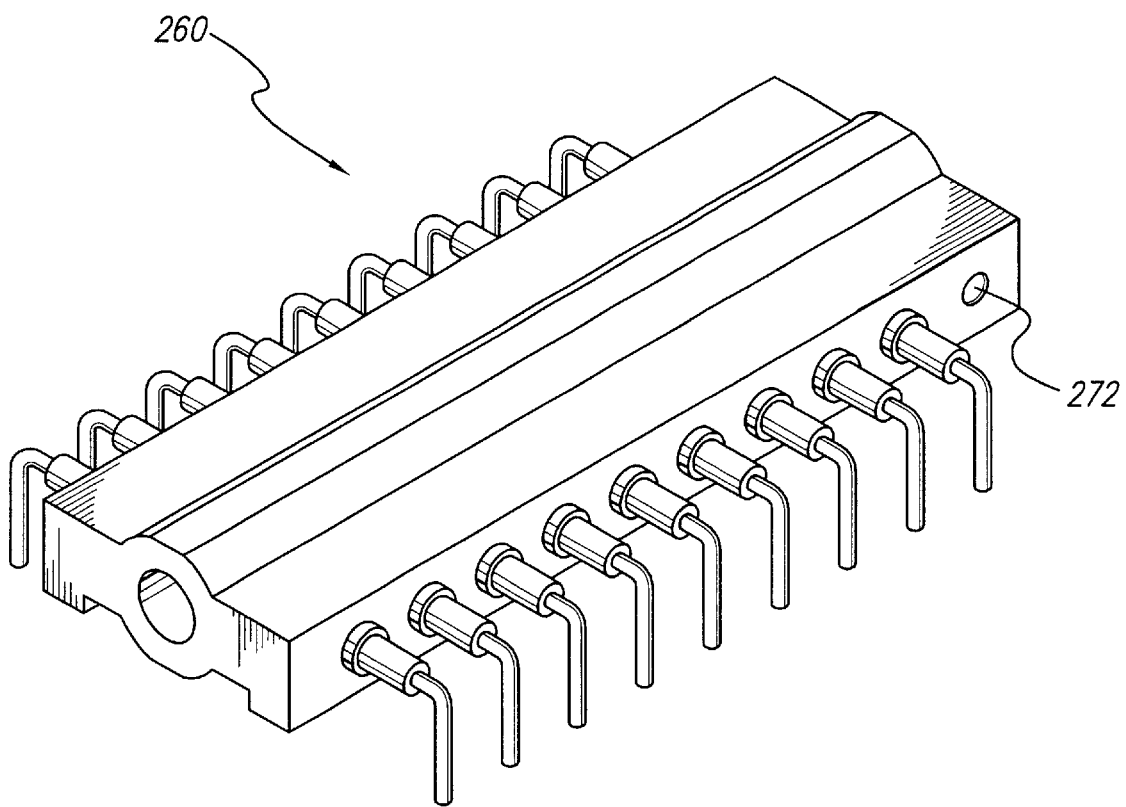
FIG. 7A is a trimetric view of a receptacle of an exemplary embodiment of the present invention.
Figure 7B:
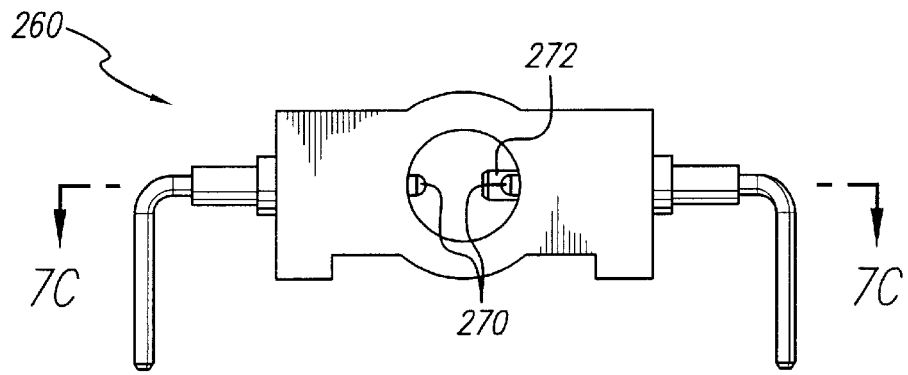
FIG. 7B is an end view of the receptacle of FIG. 7A.
Figure 7C:
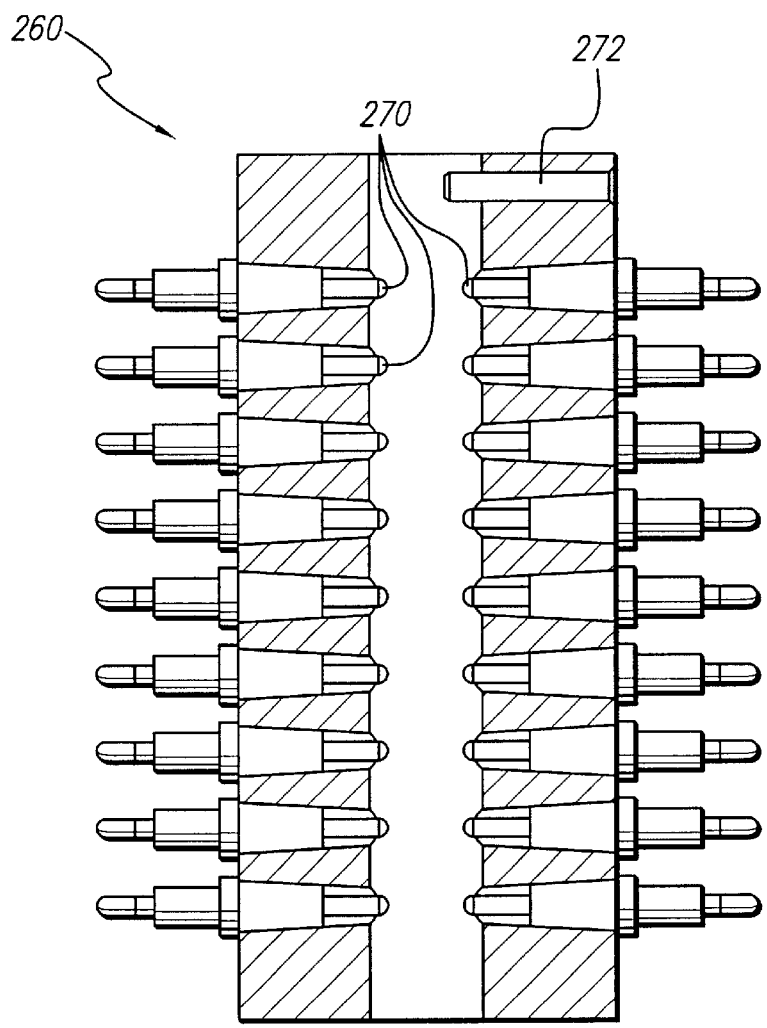
FIG. 7C is a section view through line 7C—7C shown in FIG. 7B.

Referring next to FIGS. 7A–7C, contacts 240 along the length of connector pin 220 make electrical contact with receptacle contacts 270 along the inside of a receptacle 260 when connector pin 220 is inserted into receptacle 260. Receptacle contacts 270 are, in turn, electrically connected to wires leading either to another lead/cable, such as lead extension 120, percutaneous extension 132, or external cable 134, or to an electrical device, such as IPG 100 or trial stimulator 140. Receptacle contacts are typically made of, for instance, stainless steel, nickel-plated stainless steel, gold-plated beryllium copper, titanium, tantalum, or noble metal(s) such as platinum or platinum/iridium.

In the embodiment depicted in FIGS. 7A–7C, receptacle contacts 270 comprise spring-loaded pins, also known as spring plungers. These spring-loaded pins typically comprises a helical compression spring biased into a position that causes the distal tip of spring-loaded pin to protrude into receptacle 260. During insertion into receptacle 260, connector pin 220 pushes the distal tip of the each spring-loaded pin in a proximal direction, which in turn compresses the spring within each spring-loaded pin. Once connector pin 220 is fully inserted, the distal tip of each spring-loaded pin is pushed distally by its spring into contacts 240 in the side of connector pin 220. Suitable spring-loaded pins are commercially available from Interconnect Devices, Inc. of Kansas City, Kans.

As is readily apparent from FIGS. 7A and 7C, in some preferred embodiments, eighteen receptacle contacts 270 are provided, which would electrically connect to eighteen pin contacts 240. As mentioned earlier, providing additional contacts allows enhanced stimulation protocols and/or additional channels for other purposes, such as for feedback.

A preferred connector pin 220 for use with the receptacles depicted in FIGS. 7A–7C is shown in FIGS. 8A and 8B. Between two rows of contacts 240 is a hooked groove 280. On the side of connector pin 220 opposite hooked groove 280 is another groove (not shown), which may or may not be hooked. As shown in FIG. 8B, when connector pin 220 is inserted, it should be rotated so that grooves 280 align with the distal ends of receptacle contacts 270. This will also allow groove 280 to slide over locking pin 272 (FIGS. 7B and 7C).

Locking pin 272 guides connector pin 220 during insertion into receptacle 260. As locking pin 272 reaches hook 282 of groove 280, connector pin 220 is turned as locking pin 272 slides along hook 282. As the locking pin reaches the end of groove 280, at the tip of hook 282, all contacts 240 become properly connected to their respective receptacle contacts 270. Therefore, if the connector pin 220 is intended to be inserted in only one orientation, it is preferable that only one groove 280 include a hook 282. In this preferred embodiment, therefore, contacts 240 are advantageously prevented from touching receptacle contacts 270 until all contacts are appropriately aligned.

In another alternative, the receptacle 260 shown in FIGS. 9A–9D is used. Receptacle contacts 270 are comprised of leaf-springs secured to the receptacle. These leaf-springs are preferably thin pieces of metal formed into a shape that allows the springs to return to their original position after moderate displacement. Thus, receptacle contacts 270 of FIGS. 9A–9D are biased to make reliable electrical connections with contacts 240 when connector 220 (FIG. 10) is fully inserted, yet the leaf-springs may be displaced slightly to allow easy insertion of the connector. Furthermore, the configuration of leaf-spring receptacle contacts 270 aids in holding connector pin 220 in place after insertion. (As expected, connector pin 220 of FIG. 10 comprises two rows of contacts 240, with the second row positioned on the side opposite the contacts 240 visible in FIG. 10.)

Figure 9A:
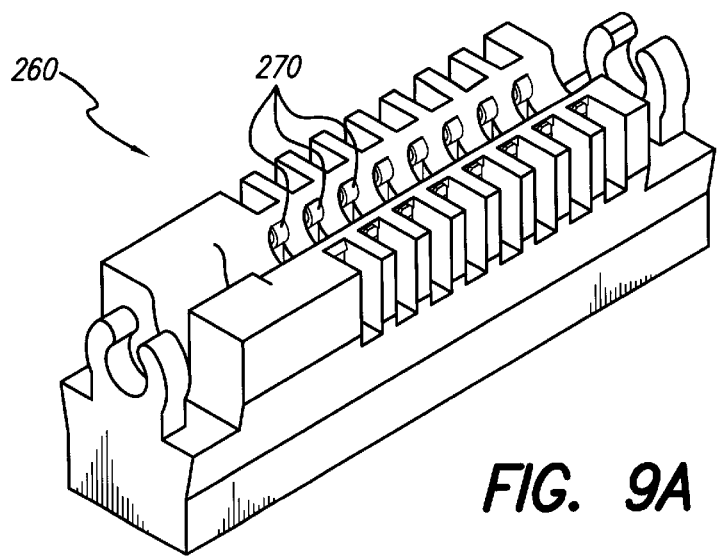
FIG. 9A is a trimetric view of a receptacle of an exemplary embodiment of the present invention.
Figure 9C:
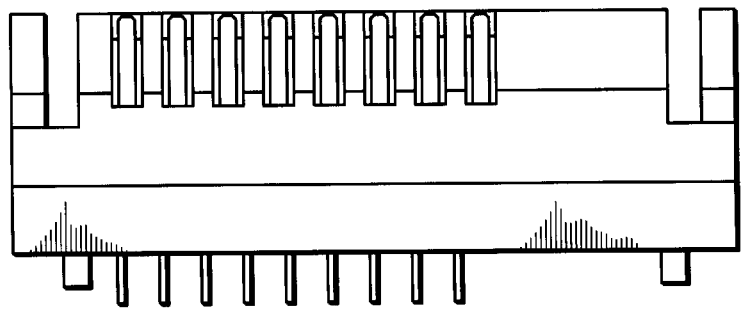
FIG. 9C is a side view of the receptacle of FIG. 9A.
Figure 9B:
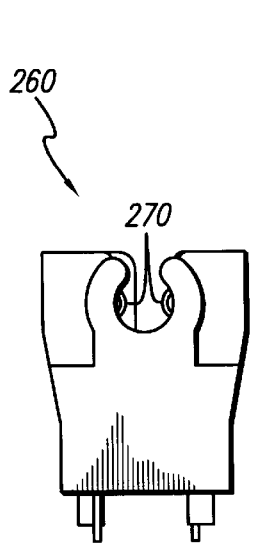
FIG. 9B is an end view of the receptacle of FIG. 9A.
Figure 9D:
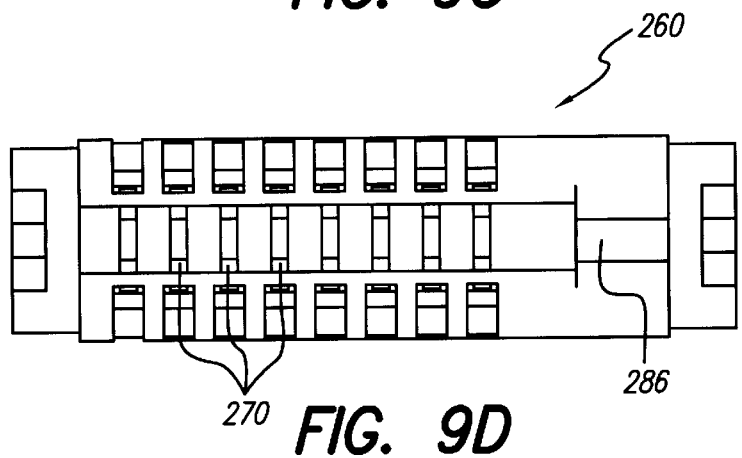
FIG. 9D is a top view of the receptacle of FIG. 9A.
Figure 10:
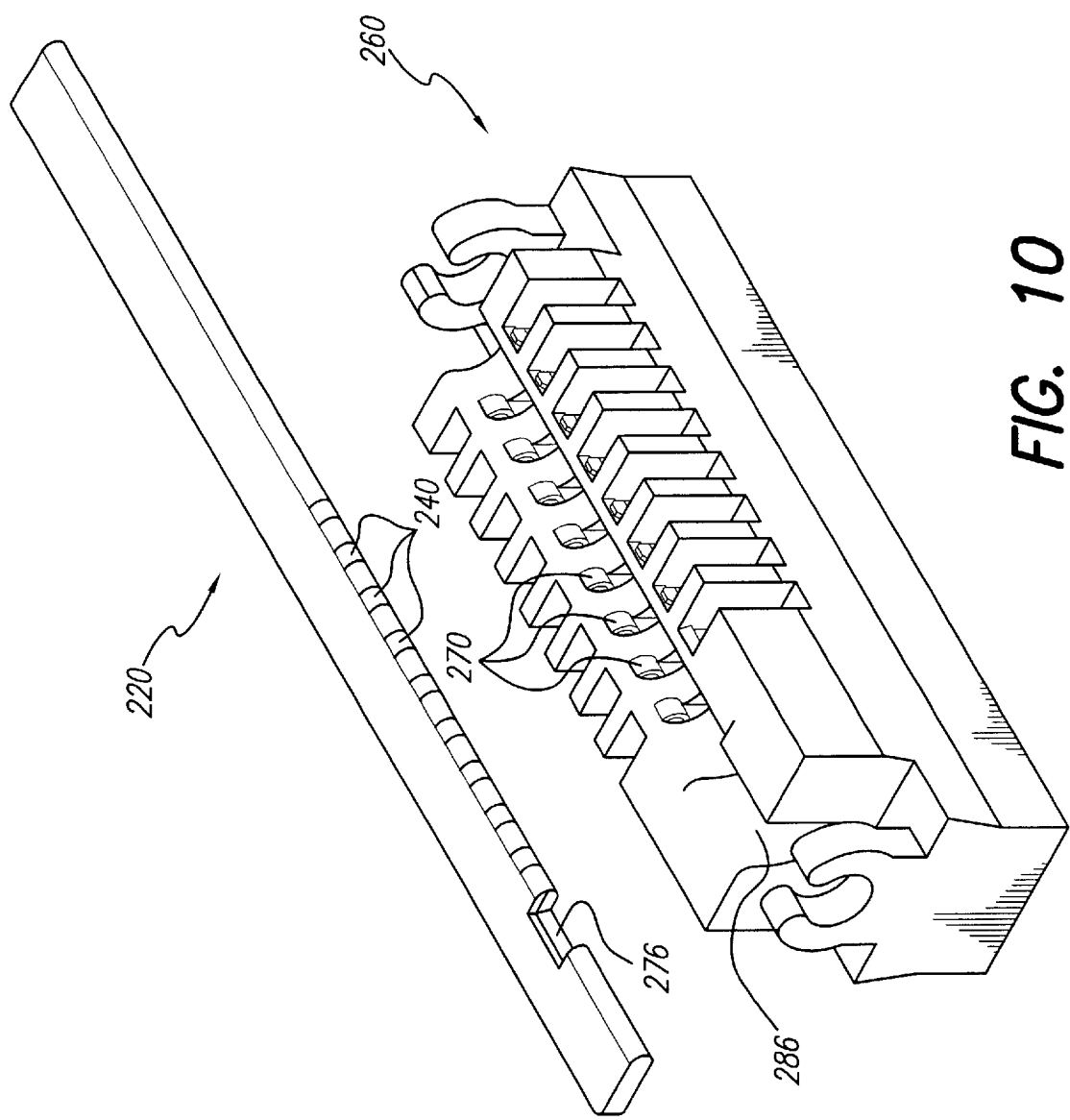
FIG. 10 is a trimetric view of the receptacle of FIGS. 9A–9D and a connector pin of an exemplary embodiment of the present invention.

As best seen in FIG. 9D and FIG. 10, receptacle 260 and connector pin 220 are keyed to allow insertion of the connector pin in only one orientation. A channel 286 is provided in receptacle 260 that accepts the section of connector pin 220 with a notch 276. Since connector pin 220 will not fit into receptacle 260 in any other orientation, contacts 240 are advantageously prevented from touching the leaf-spring receptacle contacts 270 until all contacts are properly aligned.

Figure 11C:
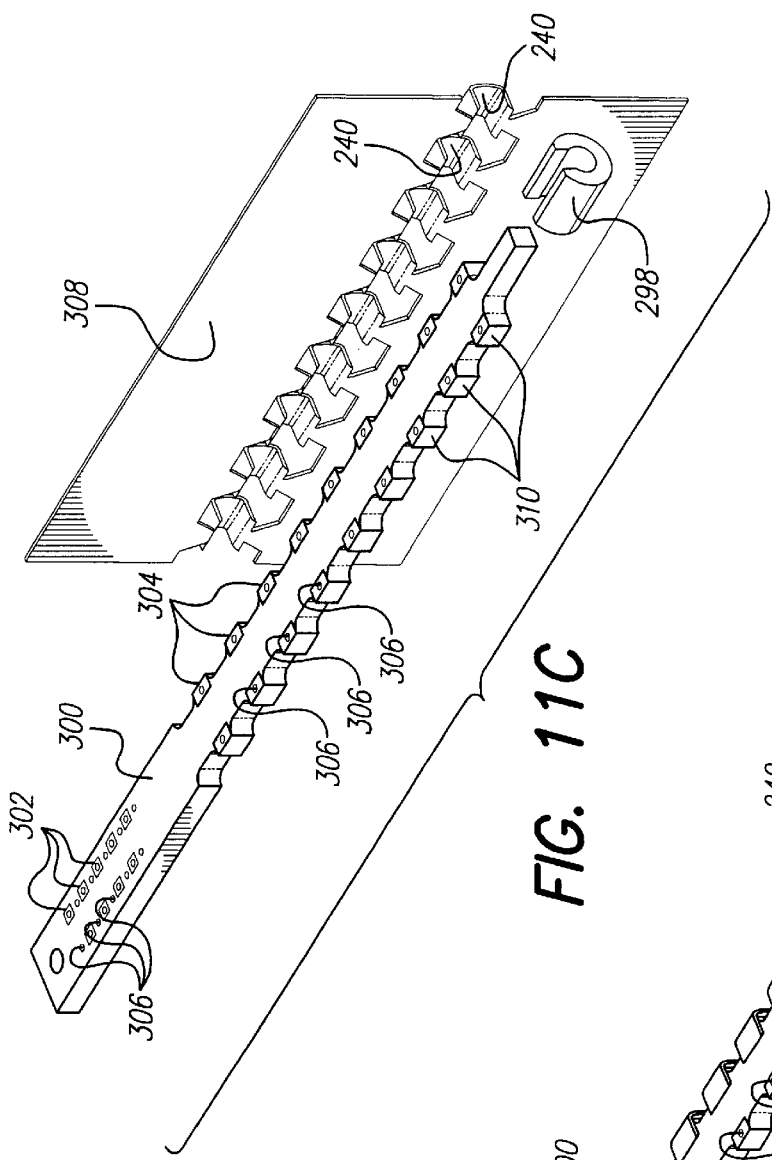
FIG. 11C is an exploded trimetric view of selected components of the pin of FIG. 11A.

In yet another alternative, the connector pin 220 shown in FIGS. 11A and 11B is used. Once again, connector pin 220 comprises two rows of contacts 240, with the second row positioned on the side opposite the contacts 240 visible in FIGS. 11A and 11B. Connector pin 220 of FIGS. 11A and 11B is comprised of an outer portion 290, which is preferably but not necessarily molded of a thermoplastic polymer material, such as Lexan® PC polycarbonate resin, Ultem® polyetherimide (PEI), or the like. Outer portion 290 may alternatively be cast, in which case, outer portion 290 may be made of an epoxy resin material, such as Hysol® resin, or the like.

Outer portion 290 preferably has a grooved portion 292, which advantageously provides for a secure hold to the lead cable or carrier 116 (not shown) and a strain relief portion (not shown) that is preferably overmolded to the grooved portion and lead cable. Additional grooves, or alternative configurations, such as dimples, spirals, etc., may be used.

Contact portion 294 and end portion 296 are configured to be inserted into a receptacle. End portion 296, when used, preferably provides a means for activating the electrical connections between the contacts 240 in connector pin 220 and the receptacle contacts 270 with, e.g., an electrically or mechanically activated switch 298 or other means known in the art. Alternatively, connector pin 220 may incorporate a grooved hook or the like, as described above, to prevent electrical contact until the pin and receptacle contacts are properly aligned. In addition, contact portion 294 is preferably keyed, such as with a flat top and rounded bottom as shown, to allow insertion of the connector pin in only one orientation.

Figure 11D:
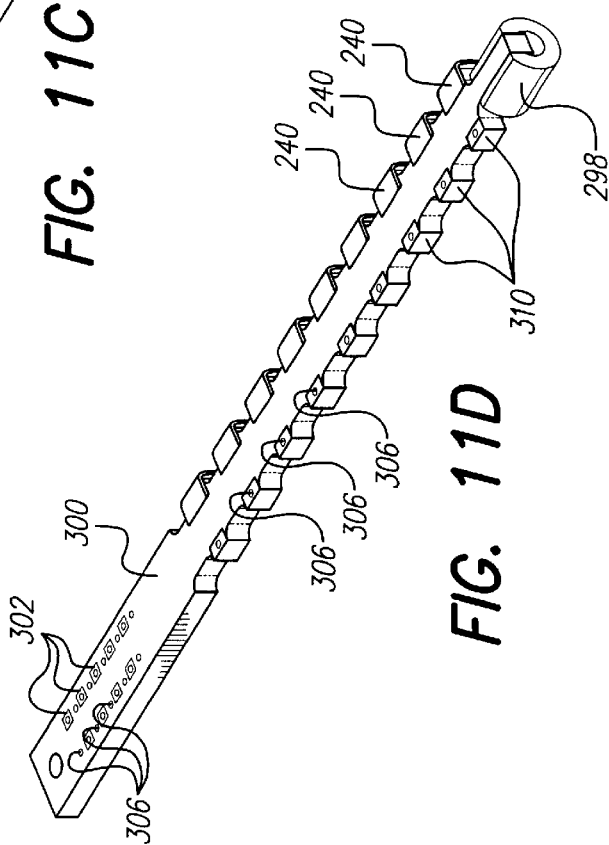
FIG. 11D is a trimetric view of selected assembled components of the pin of FIG. 11A.

Internal to connector pin 220 is preferably a printed circuit board (PCB) 300 (FIGS. 11C and 11D), made using techniques known in the art of PCB manufacturing. For instance, PCB 300 may be made of multiple layers, each containing a number of the traces (e.g., gold plated copper traces) on its top and bottom which carry electrical current from conductor pads 302, where the lead conductors are soldered, to contact pads 304, where the contacts 240 are soldered. To do this, conductor pads 302 and contact pads 304 preferably include plated-through holes 306, made via traditional means known in the PCB art, e.g., by ionic deposition, electroplating, or the like. Conductor pads 302, contact pads 304, and the material deposited in the plated-through holes 306 is preferably gold or other conductive metal.

Contacts 240 are preferably manufactured by stamping the desired contact shape out of a sheet 308 of material, such as stainless steel, nickel-plated stainless steel, gold-plated beryllium copper, titanium, tantalum, or noble metal(s) such as platinum or platinum/iridium. Contacts 240 are soldered to contact pads 304, then removed from sheet 308 via bending, breaking, trimming, or the like. Alternatively, contacts 240 may be removed from sheet 308 prior to soldering the contacts to contact pads 304.

Alternatively, contacts 240 could be made by depositing gold or other conductive metal at PCB edges 310, similar to depositing in the plated-through holes 306 extending through the PCB. This would make sheet 308 unnecessary, and contacts would not need to be soldered to the contact pads or removed from the sheet. When this method is used, edges 310 are preferably, but not necessarily, rounded from top to bottom, to better conform with the shape of outer portion 290.

Switch 298 may be a ring or similar structure that fits at the end of PCB 300. If switch 298 is intended to be an electrical switch, it is preferably plated with, e.g., gold, and soldered, molded into, or similarly attached to PCB 300. In one alternative, a trace on one of the layers of PCB 300 electrically connects a conductor pad 302 to switch 298. In another alternative, receptacle 260 has one or more receptacle contacts 270 that are electrically activated by switch 298. For instance, two specialized contacts within the connector receptacle may contact switch 298, thereby completing a circuit that activates all electrical connections between pin contacts 240 and receptacle contacts 270. In these cases, switch 298 is preferably smaller in diameter than pin contacts 240 to prevent unintended contact between switch 298 and receptacle contacts 270. Other alternatives are possible, such as a mechanical switch mentioned earlier. It is preferable that switch 298 is activated (by closing a circuit or other method), thus electrically activating the device, only after all pin contacts and receptacle contacts are aligned.

As mentioned earlier, outer portion 290 is preferably provided by placing the finished subassembly of PCB 300, contacts 240, switch 298, conductor pads 302 with wires attached, etc. into a mold and molding, via insert molding or other molding method known in the art, outer portion 290. Connector pin 220 of FIGS. 11A and 11B may advantageously be used with the receptacles 260 previously described, with slight modifications made to accommodate, e.g., end portion 296, switch 298, and/or the flat top of contact portion 294. Upon reading the information herein, those of skill in the art will be capable such modifications.

An additional advantage of the connector pin 220 and receptacle 260 combinations disclosed herein are their toolless operation. Although not a required feature, tool-less electrical connections between connector pin 220 and receptacle 260 will result in less surgical time, and less opportunity for error. The present invention provides small connector pins 220, that are preferably configured to provide tool-less connections to receptacles 260 and are preferably keyed to allow only one connection orientation.

While the invention herein disclosed has been described by means of specific embodiments and applications thereof, numerous modifications and variations could be made thereto by those skilled in the art without departing from the scope of the invention set forth in the claims. For instance, more than two rows of contacts 240 on connector pin 220 may make electrical connection with more than two rows of receptacle contacts 270 in receptacle 260. This allows for additional electrical components, such as electrodes 114, 115, and/or 115' positioned at the distal end of cable 116, or allows for additional electrode arrays 110 to connect to one device, such as IPG 100 or trial stimulator 140. In another variation, the rows of contacts may not be straight. For instance, the contacts may be in staggered positions around the pin, or may be arranged helically, with the contacts in the receptacle preferably arranged to coincide with the contacts along the connector pin.

What is claimed is:

1. A medical device comprising components housed within an enclosure, wherein the components are configured to carry out a desired function, the medical device further comprising:
   at least one lead terminating in at least one connector pin; and
   at least one receptacle within the enclosure for receiving the at least one connector pin;
   wherein the at least one connector pin comprises at least two rows of connector pin contacts; and
   wherein the at least one receptacle comprises at least two rows of receptacle contacts; and
   wherein the at least one connector pin is configured to be inserted into the at least one receptacle.

2. The medical device of claim 1 wherein the at least one connector pin is configured to be inserted into and secured within the at least one receptacle without the aid of a tool.

3. The medical device of claim 1 wherein the at least one receptacle is configured to accept the connector pin in only one orientation.

4. The medical device of claim 1 further comprising a switch activated by at least one of the at least one connector pin and the at least one receptacle, whereby electrical connection between the connector pin contacts and the receptacle contacts is activated.

5. The medical device of claim 1 wherein the at least one connector pin and the at least one receptacle are configured to prevent the connector pin contacts from touching the receptacle contacts until all contacts are appropriately aligned.

6. The medical device of claim 5 wherein the at least one connector pin comprises at least one groove and wherein the at least one receptacle comprises at least one pin and wherein the at least one pin is configured to fit into the at least one groove.

7. The medical device of claim 5 wherein the at least one connector pin comprises at least one notch and wherein the at least one receptacle is configured with a channel sized specifically to accommodate the at least one notch.

8. The medical device of claim 1 wherein the at least one connector pin and the at least one receptacle are configured to provide electrical connection between any two selected from the group consisting of an implantable pulse generator, a trial stimulator, an external lead cable, a percutaneous lead extension, an implantable lead extension, and a lead containing an electrode array.

9. The medical device of claim 1 wherein the receptacle contacts comprise spring-loaded pins.

10. The medical device of claim 1 wherein the receptacle contacts comprise leaf-springs.

11. The medical device of claim 1 wherein the at least one connector pin comprises at least one printed circuit board.

12. An electrical connector comprising at least one receptacle and at least one connector pin configured to mate with the at least one receptacle wherein the at least one connector pin comprises at least two rows of connector pin contacts and wherein the at least one receptacle comprises at least two rows of receptacle contacts.

13. The electrical connector of claim 12 wherein the at least one connector pin is configured to be inserted into and secured within the at least one receptacle without the aid of a tool.

14. The electrical connector of claim 12 wherein the at least one receptacle is configured to accept the connector pin in only one orientation.

15. The electrical connector of claim 12 further comprising a switch activated by at least one of the at least one connector pin and the at least one receptacle, whereby electrical connection between the connector pin contacts and the receptacle contacts is activated.

16. The electrical connector of claim 12 wherein the at least one connector pin and the at least one receptacle are configured to prevent the connector pin contacts from touching the receptacle contacts until all contacts are appropriately aligned.

17. The electrical connector of claim 16 wherein the at least one connector pin comprises at least one groove and wherein the at least one receptacle comprises at least one pin and wherein the at least one pin is configured to fit into the at least one groove.

18. The electrical connector of claim 16 wherein the at least one connector pin comprises at least one notch and wherein the at least one receptacle is configured with a channel sized specifically to accommodate the at least one notch.

19. The electrical connector of claim 12 wherein the at least one connector pin and the at least one receptacle are configured to provide electrical connection between any two medical components selected from the group consisting of an implantable pulse generator, a trial stimulator, an external lead cable, a percutaneous lead extension, an implantable lead extension, and a lead containing an electrode array.

20. The electrical connector of claim 12 wherein the receptacle contacts comprise spring-loaded pins.

21. The electrical connector of claim 12 wherein the receptacle contacts comprise leaf-springs.

22. The electrical connector of claim 12 wherein the at least one connector pin comprises at least one printed circuit board.

* * * * *